(12) United States Patent
Koest

(10) Patent No.: US 7,425,068 B2
(45) Date of Patent: Sep. 16, 2008

(54) METHOD FOR OPERATING AN OPHTHALMOLOGICAL ANALYSIS SYSTEM

(75) Inventor: Gert Koest, Hannover (DE)

(73) Assignee: Oculus Optikgeraete GmbH, Wetzlar Dutenhofen (DE)

(*) Notice: Subject to any disclaimer, the term of this patent is extended or adjusted under 35 U.S.C. 154(b) by 269 days.

(21) Appl. No.: 11/182,131

(22) Filed: Jul. 14, 2005

(65) Prior Publication Data

US 2006/0274269 A1    Dec. 7, 2006

(30) Foreign Application Priority Data

Jun. 7, 2005    (DE) ............... 10 2005 026 371

(51) Int. Cl.
*A61B 3/00* (2006.01)

(52) U.S. Cl. ....................... 351/246

(58) Field of Classification Search ............ 351/246, 351/214
See application file for complete search history.

(56) References Cited

U.S. PATENT DOCUMENTS

| 4,632,528 | A |   | 12/1986 | Yoshino et al. |         |
|-----------|---|---|---------|----------------|---------|
| 4,710,193 | A | * | 12/1987 | Volk           | 623/6.23 |
| 4,764,006 | A | * | 8/1988  | Hamano et al.  | 351/211 |
| 5,325,135 | A | * | 6/1994  | Nakamura et al.| 351/212 |
| 5,359,669 | A | * | 10/1994 | Shanley et al. | 382/11  |

(Continued)

FOREIGN PATENT DOCUMENTS

DE    43 21 796 A1    1/1994

(Continued)

OTHER PUBLICATIONS

Burkhard Dick, et al., "Interpretation of Scheimpflug Based Anterior Segment Imaging and Mapping," XP002412373, Eurotimes, [Online], 6 pgs. (Feb. 1, 2005).

(Continued)

*Primary Examiner*—Ricky L Mack
*Assistant Examiner*—Tuyen Q Tra
(74) *Attorney, Agent, or Firm*—Blakely, Sokoloff, Taylor & Zafman LLP

(57) ABSTRACT

The present invention relates to a method for operating an ophthalmological analysis system having a slit projection unit for slit illumination of the eye and a Scheimpflug camera for taking digitized sectional images of the eye, slit projection unit and Scheimpflug camera being mounted so that they may pivot jointly rotating around an axis which is essentially coincident with the optical axis of the eye. In a first position of slit projection unit and Scheimpflug camera, a recording of a sectional image of the eye is made and stored as the first image data set. Subsequently, slit projection unit and Scheimpflug camera are pivoted rotating at least once and fixed in this particular subsequent (second, third, fourth, . . . ) position. In the particular subsequent (second, third, fourth, . . . ) position of slit projection unit and Scheimpflug camera, a recording of a sectional image of the eye is made and stored as the subsequent (second, third, fourth, . . . ) image data set. A multidimensional description model of at least one component of the eye is derived through image data analysis of the different image data sets in a digital image data analysis device and stored as the resulting data set. The resulting data set is output in suitable form to a data output device.

18 Claims, 11 Drawing Sheets

U.S. PATENT DOCUMENTS

| | | |
|---|---|---|
| 5,886,768 A | 3/1999 | Knopp et al. |
| 6,588,903 B2 | 7/2003 | Rathjen |
| 7,111,938 B2 * | 9/2006 | Andino et al. ............. 351/212 |
| 2002/0101567 A1 | 8/2002 | Sumiya |
| 2003/0053025 A1 * | 3/2003 | Turner et al. ............. 351/205 |
| 2003/0063258 A1 * | 4/2003 | Torii et al. ............. 351/214 |
| 2004/0021826 A1 * | 2/2004 | Sarver et al. ............. 351/212 |
| 2005/0057722 A1 | 3/2005 | Koest |
| 2005/0122474 A1 | 6/2005 | Koretz |
| 2005/0146685 A1 * | 7/2005 | Hanaki et al. ............. 351/200 |

FOREIGN PATENT DOCUMENTS

| | | |
|---|---|---|
| DE | 198 57 001 A1 | 6/2000 |
| DE | 103 07 741 A1 | 9/2004 |
| EP | 0 933 060 B1 | 7/2000 |
| EP | 1 074 214 A1 | 2/2001 |
| EP | 1 275 337 A2 | 1/2003 |
| GB | 2 112 171 A | 7/1983 |
| WO | WO 02/45578 A1 | 6/2002 |

OTHER PUBLICATIONS

"Die Neue Sicht in unser Auge," Augenlicht Visioncare, [Online], XP002412374 (2005).

V. Dragomirescu, et al., Development of a New Equipment for Rotating Slit Image Photography According to Scheimpflug's Principle, XP000613975, Interdisciplinary Topics in Gerontology, pp. 118-130 (Jan. 1978).

European Serch Report for Counterpart Application No. 0600902839-1265, 12 pgs. (Jan. 15, 2007).

* cited by examiner

METHOD FOR OPERATING AN OPHTHALMOLOGICAL ANALYSIS SYSTEM

FIELD

The present invention relates to a method for operating an ophthalmological analysis system.

BACKGROUND

Devices for eye examination having Scheimpflug cameras are known from the related art and are typically used for diagnosing the anterior chamber of the eyeball. These devices allow a special form of slit lamp examination, the illuminated plane of the eye being recorded using the Scheimpflug camera. These devices for eye examination also have a slit projection unit for slit illumination of the eye, in addition to the Scheimpflug camera. Slit projection units of this type are also known from the related art. The principle of the slit projector is based on the fact that the refractive media in the eye are not transparent, but rather significant scattering occurs in them, particularly in the shortwave component of visible light. This results in a sharply bundled light beam, i.e., the projected light slit, which is sent through the optic media of the eye, being visible upon lateral observation. This effect is similar to the light refraction as light from a headlight passes through fog. Since the different components of the eye have light scatters of different strengths, statements about the structure of the eye may be made through these examinations. A slit-shaped light bundle of high light brightness and the highest possible color temperature is used for the slit illumination.

The plane in the eye illuminated using the slit projection unit is recorded using the Scheimpflug camera. Such a Scheimpflug camera is a camera which fulfills the Scheimpflug condition. The Scheimpflug condition requires that the projection plane which is the plane in the eye illuminated using the slit projection unit here, intersects the main plane of the lens system and the image plane between a shared axis. By tilting the image plane in relation to the main plane of the lens system, the projection plane may be in any arbitrary spatial position, pixels able to be registered in the depth of field zone which may not be imaged equally sharply with a perpendicular projection plane.

Typically, the images recorded using the Scheimpflug camera are displayed to the technician in suitable form, for example, as printouts, the technician then having to judge on the basis of his experience whether there are pathological changes on the examined part. This type of evaluation of the Scheimpflug photograph has the disadvantage, however, that very great experience is necessary to recognize specific clinical pictures. In addition, clinical pictures and changes which have a three-dimensional appearance may be recognized only with great difficulty or not at all.

SUMMARY

On the basis of this related art, it is therefore the object of the present invention to suggest a method for operating an ophthalmological analysis system which provides very good examination results with simple handling.

This object is achieved by a method according to the teaching of claim 1.

Advantageous embodiments of the present invention are the object of the subclaims.

The method according to the present invention is based on the main idea of using a slit projection unit for slit illumination of the eye and a Scheimpflug camera for recording sectional images of the eye, which may be pivoted jointly rotating around an axis. The pivot axis of Scheimpflug camera and slit projection unit are essentially coincident with the optical axis of the eye in this case. In this way, in the framework of a series of measurements, Scheimpflug photographs may be made in different planes of the eye, so that these Scheimpflug photographs, which are each two-dimensional, together contain three-dimensional information about the structure of the eye.

According to the present invention, the Scheimpflug photographs are taken in digitized form. i.e., each Scheimpflug photograph of a sectional plane through the eye is stored as an individual image data set. This digitized recording technology allows a digital image data analysis, so that the structure of the eye and/or the structure of components of the eye may be derived from the different image data sets in an image data analysis device. The multidimensional description model of the examined component of the eye obtained in this case is stored as the resulting data set. This resulting data may subsequently the displayed in suitable form, for example, as a three-dimensional geometry model on a data output device, such as a display screen.

The type of examinations which are performed on human eye using the method according to the present invention, particularly the components of the eye which are examined, is arbitrary in principle. According to a first preferred method variation, the method is used to derive the axial length of the eye between cornea and retina. In this case, the distance which lies between the point of entry of the light beam at the apex of the cornea to the point of incidence on the retina is to be understood as the axial length of the eye. The axial length value is particularly significant for calculating artificial intraocular lenses, which are inserted into the eye in an operation, because the refractive power of the intraocular lenses must be selected so that a sharp image arises on the retina. Since all other values for calculating an intraocular lens (anterior chamber depth, corneal refractive power, etc.) may also be determined using the ophthalmological analysis system having rotatable Scheimpflug camera, deriving the axial length of the eye using the method according to the present invention is of special advantage, since this value could only be determined using very cumbersome measurement methods (ultrasonic measurement, interference measurement) in separate examination devices until now. By determining the axial length of the eye in the method according to the present invention, as a result, all measured values necessary for calculating an intraocular lens are determined using one single examination device, which represents a significant simplification.

To determine the axial length of the eye, suitable examination systems, for interference measurement or for ultrasonic measurement, for example, may be integrated accordingly into the ophthalmological analysis system provided for the sectional image examination. Alternatively to this, the measurement of the axial length of the eye is also possible through analysis of the data sets containing the sectional images. In order to be able to determine the axial length of the eye as simply as possible from the data sets containing the sectional images, the eye may be imaged over its complete depth from the cornea up to the retina in the depth of field range of the Scheimpflug camera. This may particularly be achieved if the Scheimpflug camera is set with a very flat recording angle in relation to the main axis of the eye.

According to a second method variation of the examination method according to the present invention, the thickness of the natural eye lens of the eye or the position of an artificial intraocular lens, which replaces the natural eye lens, in the eye may be derived from the image data sets. This type of examination is of great significance for the accommodation capability of the eye, since the natural eye lens may have its thickness deformed, through which the eye may adapt to different object sizes. This accommodation is implemented if the natural eye lens is replaced by an artificial intraocular lens through suitable adjustment of the intraocular lens in relation to the retina.

In order to be able to examine the accommodation behavior of the natural eye lens and/or the artificial intraocular lens, it is especially advantageous if the muscle provided for deforming the natural eye lens and/or for adjusting the intraocular lens replacing the natural eye lens may be put in different states of excitation during a series of measurements. In this way, the deformation of the eye lens and/or the adjustment of the intraocular lens may be determined as a function of the excitation of the accommodation muscle in the eye through the image data analysis according to the present invention.

In order to be able to implement the desired excitation of the accommodation muscle having different states of excitation as the examination method is performed, the fixation mark provided in the analysis system may be used. This fixation mark, such as a point of light, is sighted by the patient during the examination using the eye to be examined in order to fix the eye in a defined position in this way. Since the eye unintentionally attempts the sharp imaging of the fixation mark on the retina through accommodation of the natural eye lens and/or adjustment of the artificial intraocular lens, by changing the actual or virtual distance between eye and fixation mark, the accommodation muscle may be excited variably in the way desired. For example, if the fixation mark is positioned in a near point, i.e., at a distance of approximately 30 cm, in front of the eye, the eye lens or the intraocular lens is deformed or adjusted, respectively, by the accommodation muscle in such way that the fixation mark is imaged sharply on the retina. If the fixation mark is subsequently positioned in a far point, for example, at a virtual distance of 5 m in front of the eye, the muscle tension of the accommodation muscle changes accordingly, so that through the altered thickness of the eye lens and/or through the altered position of the intraocular lens, the fixation mark is again imaged sharply on the retina. As a result, by changing the distance between eye and fixation mark, one has the possibility of exciting the accommodation muscle in the way desired.

Changing the actual distance between eye and fixation mark requires a device design which is often only to be implemented with difficulty, since a device having an axial length of multiple meters is extraordinarily cumbersome, for example. Therefore, varying the distance between eye and fixation mark only virtually by positioning at least one lens in the beam path between fixation mark and eye is preferable. In other words, this means that the actual distance between eye and fixation mark remains unchanged. By positioning a lens, the fixation mark may be projected on a virtual image plane, however, so that the eye lens and/or the intraocular lens is no longer focused on the actual fixation mark, but rather on the virtual image of the fixation mark in the virtual image plane. In this way, even large virtual distances between eye and fixation mark may be simulated, without the actual distance between eye and fixation mark having to be correspondingly large.

According to a third variation of the examination method according to the present invention, the presence of a keratoconus on the cornea may also be derived through analysis of the image data sets. Such a keratoconus represents a deformation of the cornea caused by illness, which causes malfunctions of the optical system in the eye. This deformation is caused by thinning in the cornea, so that the cornea thus typically deforms conically because of the internal pressure in the eye.

In order to be able to derive the presence of a keratoconus, according to first variation, the three-dimensional graph of the corneal thickness is derived from the image data sets. If variations above a specific tolerance limits are detected in this three-dimensional graph of the corneal thickness, the presence of a keratoconus may be assumed.

Alternatively and/or additionally to determining the graph of the corneal thickness, the three-dimensional geometry of the corneal anterior face may be derived from the image data sets. If the corneal anterior face displays an essentially conical geometry, the presence of a keratoconus is again to be assumed.

When recognizing the keratoconus, it is especially advantageous in this case if comparative values are predefined in the analysis system that describe the healthy state of the cornea and/or the pathological state of the cornea in the event of keratoconus, for example. The actual values of the graph of the corneal thickness and/or the geometry of the corneal anterior face obtained after performing the examination method may then be compared to these stored comparison values in order to be able to conclude the presence of a keratoconus on the basis of the comparison result. This type of examination is of great significance, since the keratoconus represents a contraindication for many treatments, particularly the correction of faulty vision using an eximer laser.

According to a fourth method variation, the geometry of the anterior chamber of the eyeball between cornea and iris is derived from the image data sets. This type of examination is particularly significant if a phakic intraocular lens is to be implanted to supplement the remaining natural eye lens. By determining the geometry of the anterior chamber of the eyeball, it is possible for a simulation to be performed before performing the implantation operation, using which the arrangement of a phakic intraocular lens in the anterior chamber of the eyeball may be simulated. Only if the simulation shows that there is sufficient space in the anterior chamber of the eyeball to receive the planned intraocular lens will the operation for implanting the intraocular lens be performed.

According to a fifth method variation, the geometry of the iris and the directly adjoining part of the vitreous humor is derived from the image data sets. This type of examination allows the arrangement of an artificial intraocular lens in the vitreous humor in the region behind the iris to be simulated.

According to a sixth alternative method variation, the examination method according to the present invention may also be used for determining the three-dimensional geometry of clouding of the eye lens (cataract). The natural eye lens becomes more and more cloudy with increasing age, the degree of cloudiness and the geometry of the cloudiness being individually different. This cloudiness, which is referred to as cataract, interferes with the optical system of the eye, since it may result in reduced vision power and reduced contrast sensitivity, as well as increased glare sensitivity. If too strong a cloudiness of the eye lens is determined, this illness, referred to as cataract, may be treated by removing the natural eye lens and implanting an artificial intraocular lens.

It is especially advantageous if the actual values of the cloudiness geometry intrinsic for cataract recognition are compared to comparison values predefined in the analysis system, in order to be able to classify the type of the cataract by analyzing the comparison result.

According to a seventh preferred method variation, a raster screen is positioned in the region between slit projection unit and eye during a series of measurements, so that the illumination slit is divided by the raster screen into multiple slit sections. The light of the slit projection unit forms a scattered light pattern in this way, whose individual beans run along separate beam paths through the eye. By recording and analyzing the image data of the light beam paths, the refraction ratio of the eye lens, particularly the index of refraction of the tissue forming the eye lens, may be derived. In addition, it is possible, because the eye is fixed on a fixation point at infinite distance during the series of measurements using scattered light patterns, for the axial length of the eye between cornea and retina to be derived from the image data sets containing the scattered light pattern.

BRIEF DESCRIPTION OF THE DRAWINGS

The method according to the present invention is explained for exemplary purposes in the following on the basis of the drawing.

DETAILED DESCRIPTION

Figure 1:
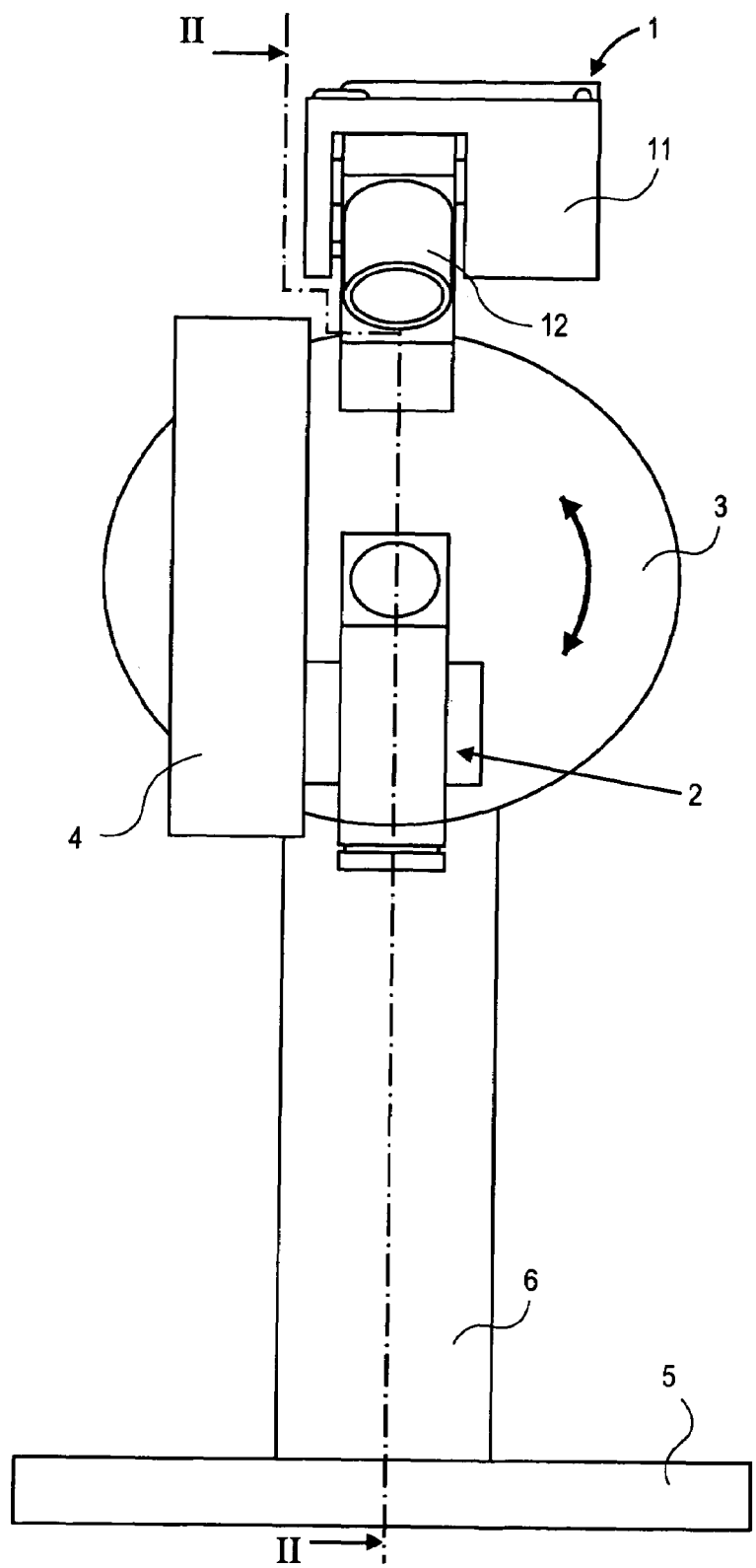
FIG. 1 shows a device for performing the method according to the present invention in a view from the front.
Figure 2:
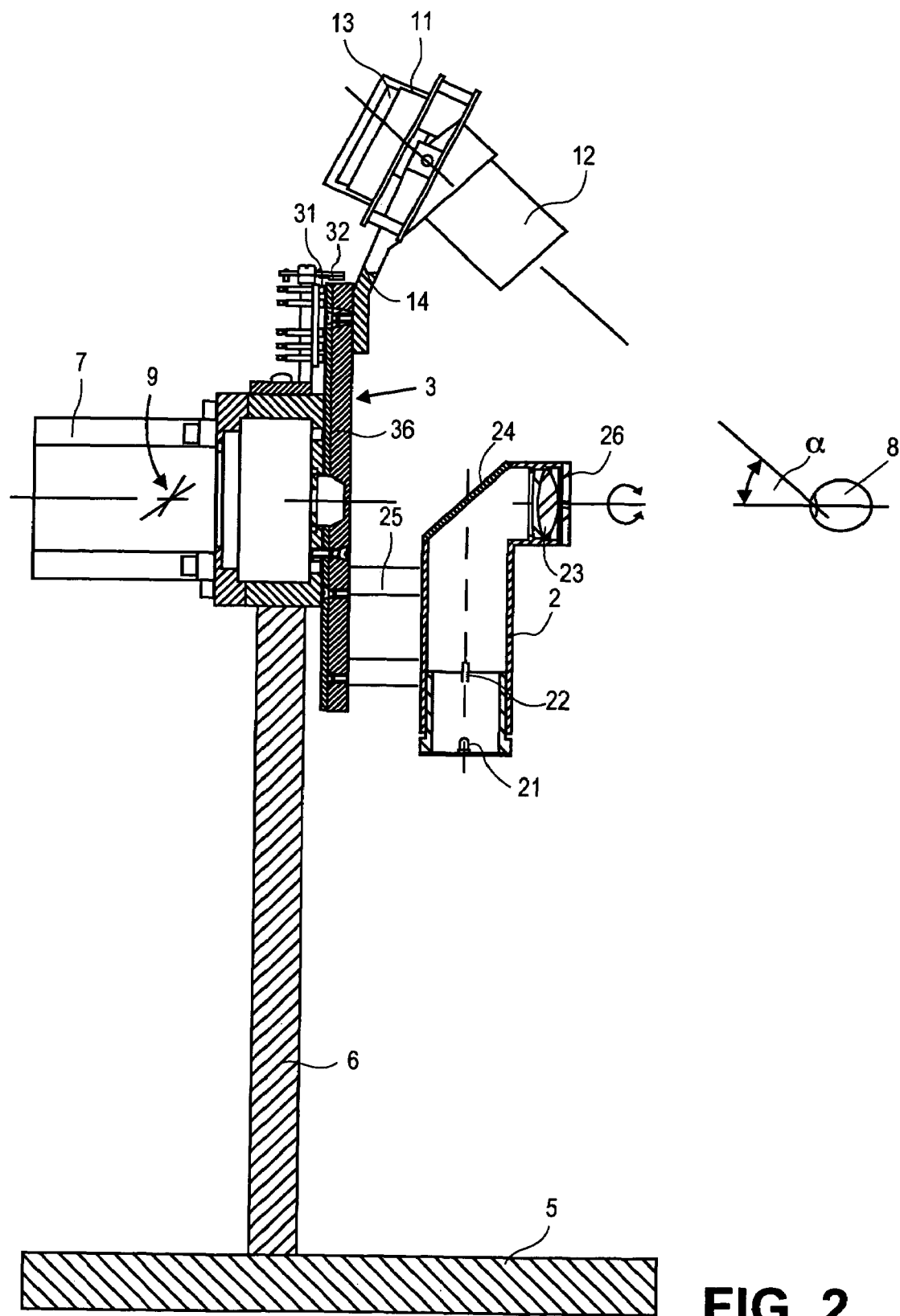
FIG. 2 shows the device shown in FIG. 1 in cross-section along the section line II-II.
Figure 3:
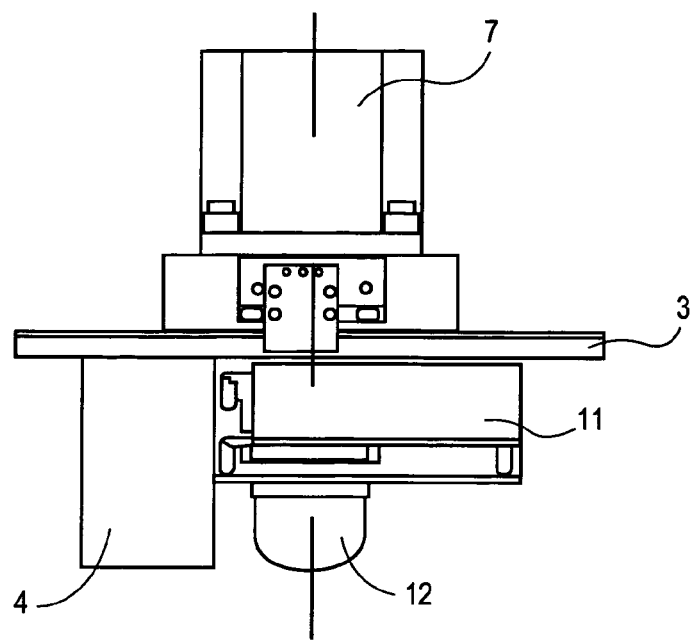
FIG. 3 shows the device shown in FIG. 1 in a view from above.
Figure 3:
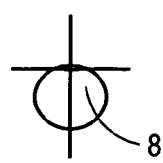
Figure 4:
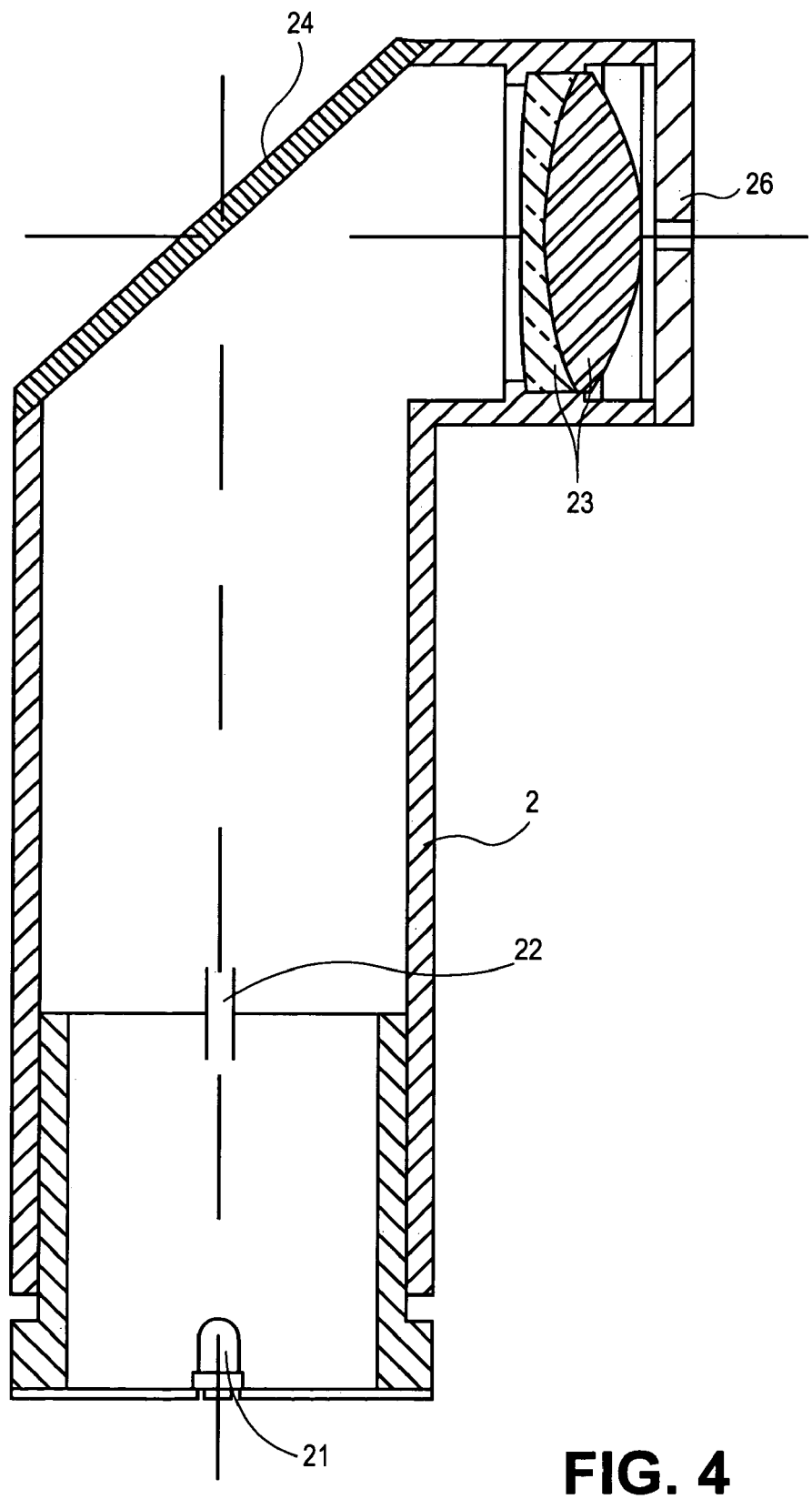
FIG. 4 shows the slit projection unit of the device shown in FIG. 1 in cross-section.
Figure 5:
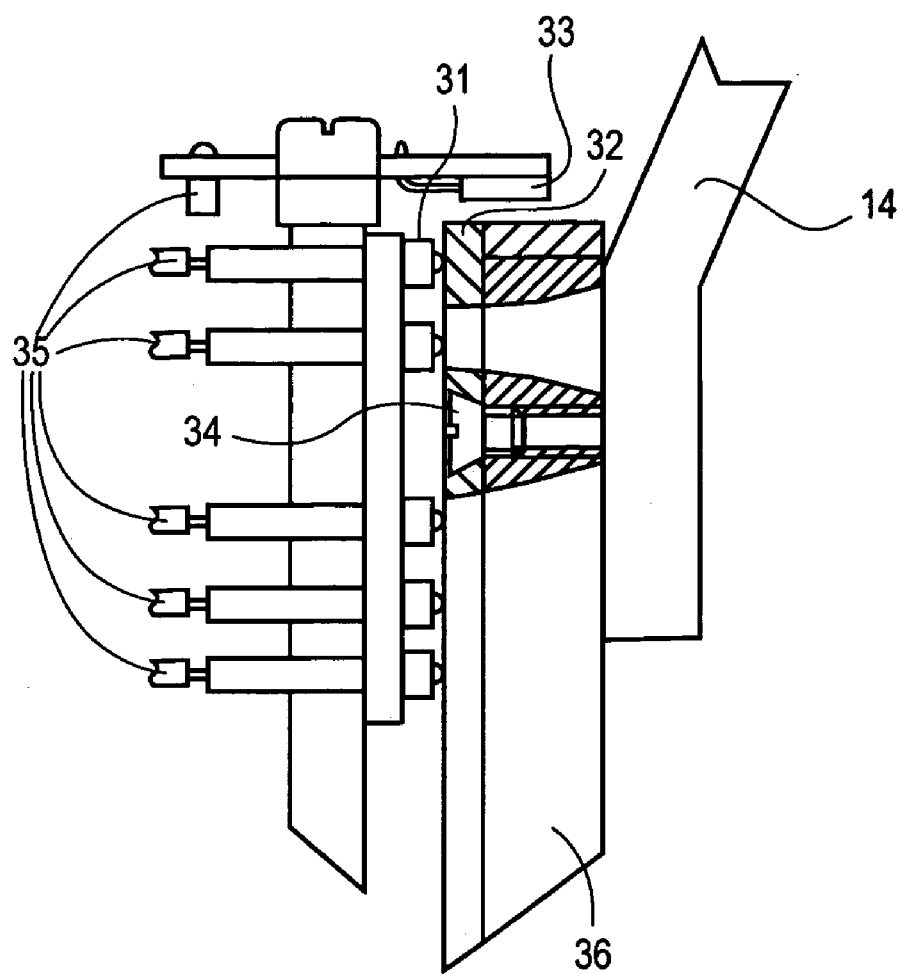
FIG. 5 shows details of a slip ring transmitter in the device shown in FIG. 1.

FIGS. 1 through 5 show a device having a Scheimpflug camera 1 and a slit projection unit 2, which are jointly attached to a rotatably mounted rotor 3. This device may be used in order to perform the method according to the present invention. Of course, however, devices implemented in other ways having a rotating Scheimpflug camera are also suitable for this purpose. If the axial length of the eye may not be derived from the image data of the sectional images taken using the Scheimpflug camera 1, for this purpose, another, correspondingly suitable examination device, such as an ultrasonic measurement device or an interference measurement device may additionally be integrated in the device having the Scheimpflug camera 1 of the slit projection unit.

The rotor 3 is mounted on a stand 6 and may be driven to rotate using a motor 7. The motor 7 is preferably a stepping motor. The attachment of slit projection unit 2 and Scheimpflug camera 1 to the rotor 3 is implemented using holders 14 and 25. The optical axis of the beams exiting from the slit projection unit 2 is coincident with the axis of rotation of the rotor 3. The eye 8 to be examined is to be positioned during the examination so that the main axis of the eye is coincident with the optical axis of the slit projector 2 and the axis of rotation of the rotor 3.

The slit projector 2 has a diode array 21 as the light source. This diode array 21 illuminates a slit screen 22, through which the slit screen is imaged via a mirror 24 in the projector lens system 23 in accordance with the Köhler imaging scheme. In addition, a raster screen 26 may be positioned in the beam path of the light slit, in order to divide the light slit into multiple image slit sections in this way, so that a scattered light pattern is projected onto the eye.

The light of the light slit bundled in the projector lens system 23 passes through the eye 8 in the plane along separate beam bundles. This plane illuminated by the light slit may be recorded using the Scheimpflug camera 1.

For this purpose, the Scheimpflug camera 1 has a camera-lens system 12, which is mounted in front of the housing 11. A CCD chip is positioned in an image plane 13 in the housing 11 of the Scheimpflug camera 1, which records digitized sectional images of the eye. In order to meet the Scheimpflug condition, the image plane 13, the main plane of the camera lens system 12, and the illuminated projection plane in the eye 8 of the subject are inclined in relation to one another so that they intersect in a shared axis 9.

The digitized sectional image recorded using the Scheimpflug camera 1 is stored after recording as an image data set and may be analyzed in a suitable image data analysis device, which is installed on an industry PC as software, for example. After recording a sectional image, the rotor 3 is pivoted one step at a time around its axis of rotation and then a further digital sectional image of the eye 8 is recorded in a further sectional plane.

Two slip rings 32 are provided for signal transmission, which are attached to the rotor 3 using screws 34. Further slip ring contacts 31 are attached to the stand 6, which are also used for signal transmission. The signals may be transmitted via the connection line 35 to the image data analysis device (not shown).

In addition to the two slip ring transmitters for signal transmission, a further three slip rings 32 and a further three slip contacts 31 are provided on the rotor 3 and on the stand 6, respectively, which are used for voltage supply. In addition, a sensor 33 is provided on the stand 6, using which the angle of rotation of the rotor 3 may be measured. Therefore, the angle of the Scheimpflug camera 1 may be determined in relation to a reference position upon each sectional image recording.

Figure 6:
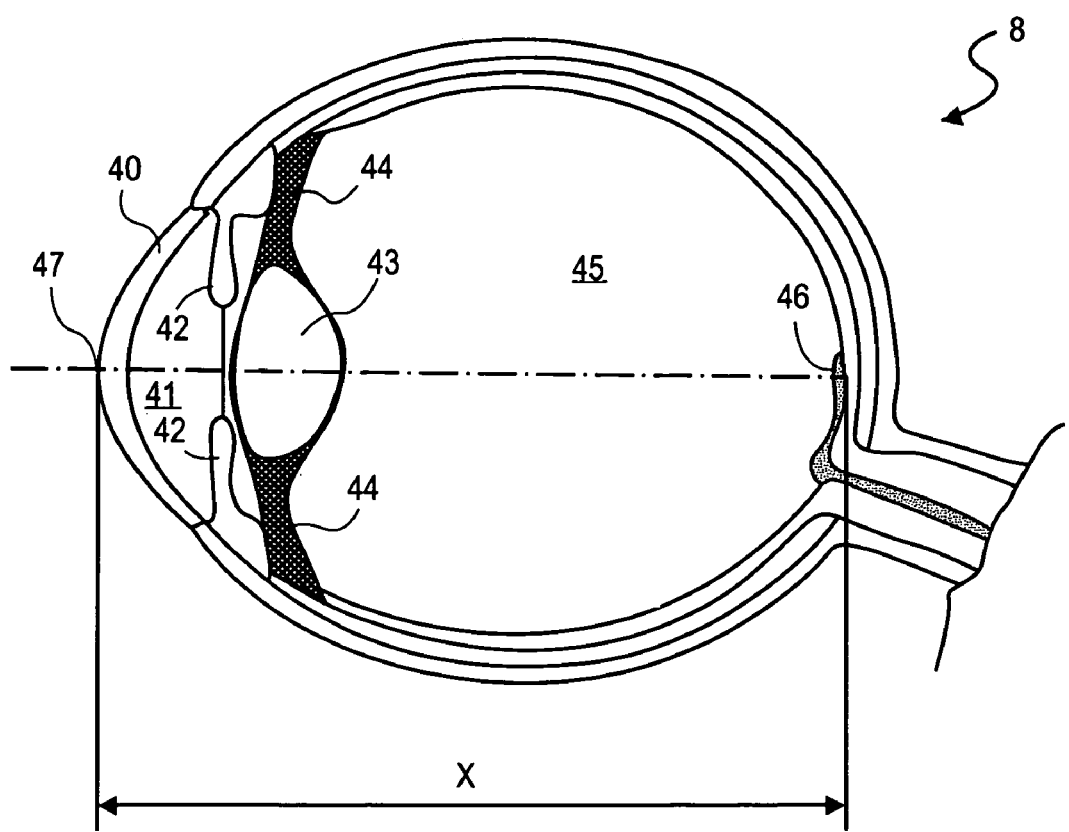
FIG. 6 shows the structure of an eye to be examined using the device shown in FIG. 1 in a schematic cross-section.

The structure of the eye 8 to be examined is schematically shown in FIG. 6. The anterior chamber of the eyeball 41, which is delimited at the rear by the iris 42, is located behind the cornea 40. The natural eye lens 43, whose shape and particularly thickness may be changed by tightening the accommodation muscle 44, is located directly behind the iris 41. After passing through the vitreous humor 45, the light beams incident in the eye 8 are focused on the retina 46. Through the examination method according to the present invention, the axial length X between the apex 47 of the cornea 40 and the retina 46 may be determined. For this purpose, multiple digitized sectional images of the eye 8 are taken in multiple angles of rotation of the rotor 3, the flattest possible image angle α being set between the slit projection unit 2 and the Scheimpflug camera 1. The image angle α is, as much as possible, to be significantly smaller than in FIG. 2. In particular, image angles α in the range from 5° to 10° are particularly suitable for determining the axis X.

Figure 7:
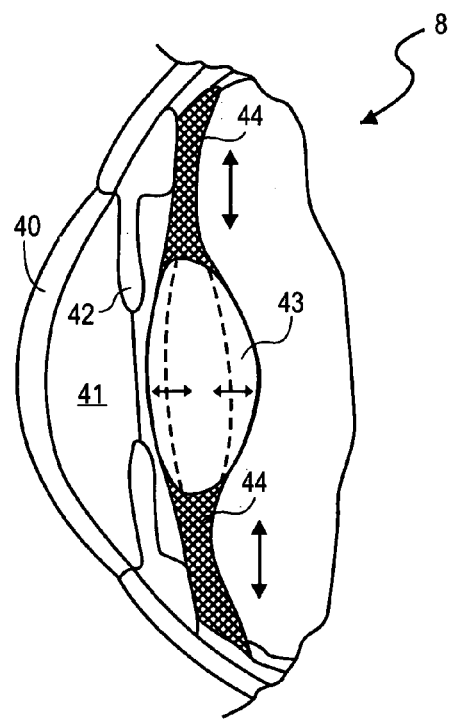
FIG. 7 shows the mode of operation of the accommodation muscle upon deformation of the eye lens in schematic cross-section.
Figure 8:
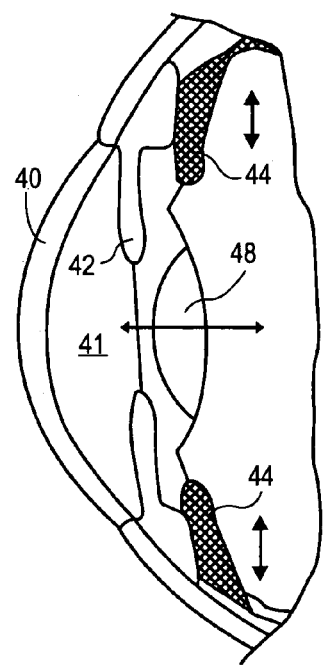
FIG. 8 shows the mode of operation of the accommodation muscle when adjusting an artificial, accommodative intraocular lens in schematic cross-section.

FIG. 7 and FIG. 8 show the possibilities for using the method according to the present invention when exciting the accommodation muscle 44 to deform the eye lens 43 (see FIG. 7) and/or to adjust an artificial intraocular lens 48, which replaces the natural eye lens 43 in the event of a cataract illness, for example. By tightening and/or relaxing the accommodation muscle 44, the eye lens 43 may be stretched and/or compressed, so that the thickness of the eye lens 43 and the curvature of the front and/or back side changes. Image planes at different distances may thus be focused on. In order to vary the excitation of the accommodation muscle 44, the examination device may be equipped with a fixation mark whose distance is changeable.

In the intraocular lens shown in FIG. 8, the focusing of the image plane is performed by displacing the intraocular lens in the direction of the main axis of the eye. This transverse displacement of the intraocular lens is implemented via an articulated suspension which works together with the accommodation muscle 44. By tightening and/or relaxing the accommodation muscle 44, the desired displacement of the intraocular lens 48 in the direction of the eye main axis is thus caused.

Figure 9:
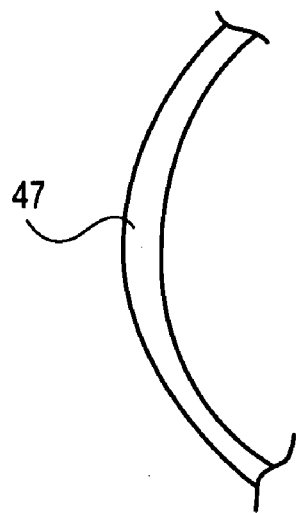
FIG. 9 shows the thickness graph of a healthy cornea in schematic cross-section.

FIG. 9 shows a healthy cornea 47 in schematic cross-section. The cornea 47 has a relatively constant thickness graph and thus curves in a circular arc.

Figure 10:
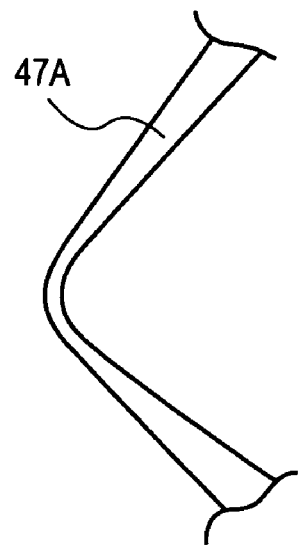
FIG. 10 shows the thickness graph of a cornea having keratoconus illness in schematic cross-section.

In contrast, a cornea 47a which has a keratoconus illness is shown in FIG. 10. Because of this illness, the cornea 47a is strongly thinned in the middle, so that the cornea 47a curves conically outward. By determining the thickness graph of the cornea 47a and/or a three-dimensional geometry, the keratoconus illness may be determined by applying the examination method according to the present invention.

Figure 11:
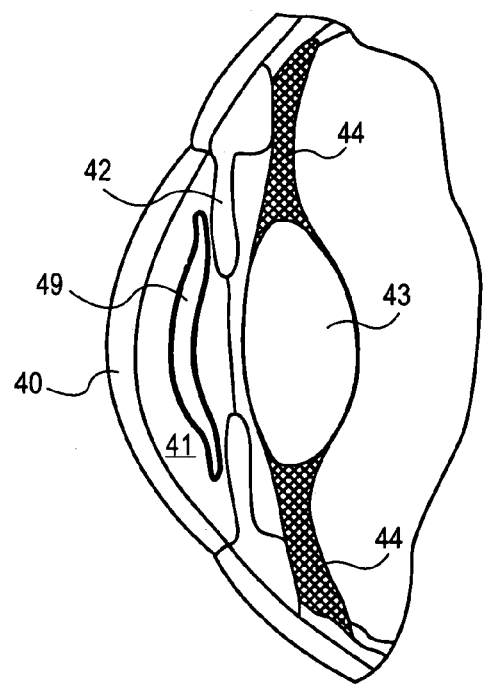
FIG. 11 shows the arrangement of a phakic intraocular lens in the anterior chamber of the eyeball of an eye in schematic cross-section.

FIG. 11 shows the arrangement of a phakic intraocular lens 49 in the anterior chamber of the eyeball 41. In order to be able to determine whether the intraocular lens 49 will have sufficient space in the anterior chamber of the eyeball 41 before implanting the phakic intraocular lens 49, the anterior chamber of the eyeball 41 may be measured three-dimensionally using the examination method according to the present invention.

Figure 12:
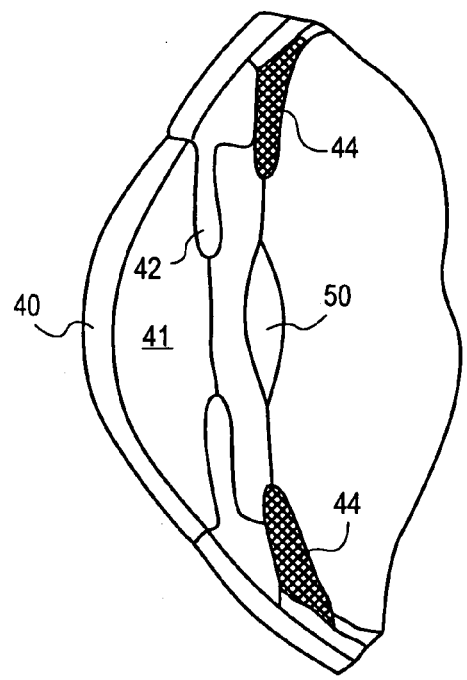
FIG. 12 shows the arrangement of an artificial intraocular lens to replace the eye lens in the region directly behind the iris in schematic cross-section.

FIG. 12 shows the arrangement of a second embodiment of an intraocular lens 50 in the vitreous humor 45 directly behind the iris 42.

Figure 13:
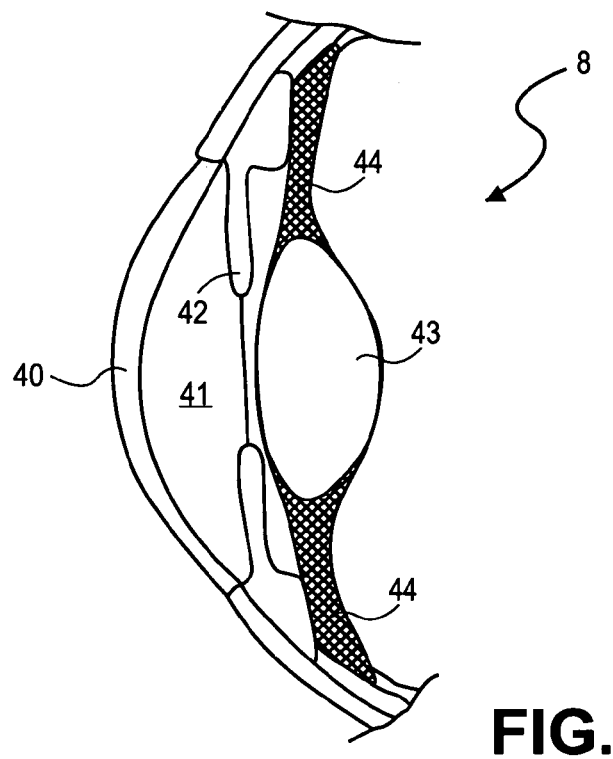
FIG. 13 shows an eye having a non-cloudy eye lens in schematic cross-section.
Figure 14:
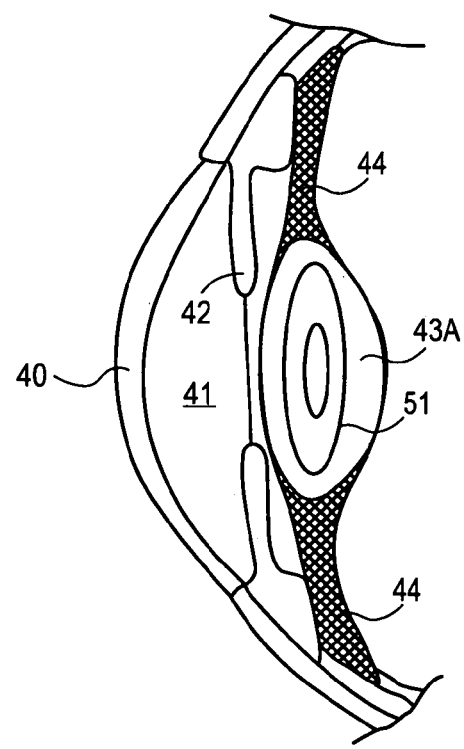
FIG. 14 shows an eye having a cloudy eye lens (cataract illness) in schematic cross-section.

FIG. 13 represents the eye lens 43 in the healthy state. The eye lens 43 is clear and has no cloudiness. In contrast to this, in FIG. 14 the eye lens 43a having a cataract illness is schematically shown. The eye lens 43a has cloudiness 51 because of the cataract illness, through which the visual power is restricted. This cloudiness 51 may be determined three-dimensionally by applying the examination method according to the present invention.

Figure 15:
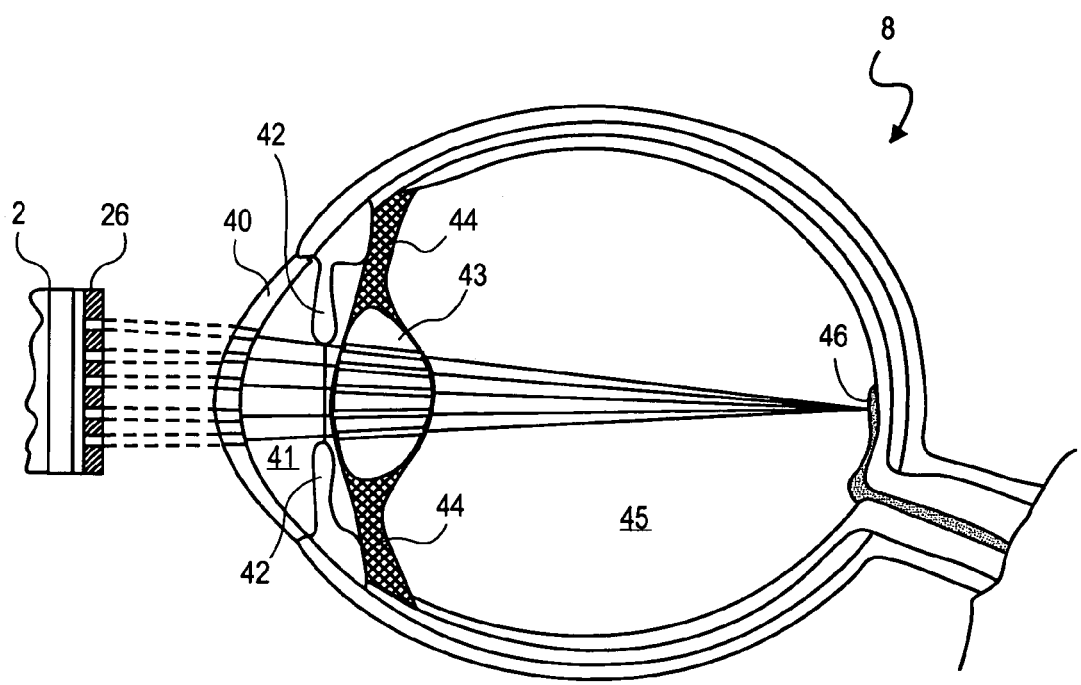
FIG. 15 shows an eye upon projection of a scattered light pattern using a raster screen in schematic cross-section.

The mode of operation of the raster screen 26 when examining the eye 8 is schematically shown in FIG. 15. Because of the division of the light slit into individual slit sections, a scattered light pattern is projected onto the eye 8, which is recorded in different sectional image planes. By analyzing this scattered light pattern in the different sectional image planes, the axial length X and the index of refraction of the eye lens 43 may be determined.

What is claimed is:

1. A method for operating an ophthalmological analysis system having a slit projection unit for slit illumination of the eye and a Scheimpflug camera for recording digitized sectional images of the eye comprising:

slit projection unit and Scheimpflug camera being mounted so they rotate jointly pivoting around an axis which is essentially coincident with the optical axis of the eye; in a first position of slit projection unit and Scheimpflug camera, a first recording of a first sectional image of the eye being made and stored as the first image data set; slit projection unit and Scheimpflug camera being pivoted rotating at least once and fixed in a particular subsequent position; in the particular subsequent position of slit projection unit and Scheimpflug camera, a second recording of a second sectional image of the eye being made and stored as the subsequent image data set; in a digital image data analysis device, a multidimensional description model of at least one component of the eye being derived through digital image data analysis of the different image data sets and stored as the resulting data set; and the resulting data set being output in suitable form to a data output device, wherein multidemensional description model of the at least one component of the eye includes a three-dimensional geometry of cloudiness of the eye lens, said cloudiness being a cataract, derived from image data sets, wherein, for the cataract recognition, the derived actual values of the cloudiness geometry are compared to comparison values predefined in the analysis system, the type of the cataract being classified as a function of the comparison result.

2. The method according to claim 1, wherein the axial length of the eye between cornea and retina is derived from the image data sets or other measurement data sets which were recorded using a further examination device integrated into the ophthalmological analysis system.

3. The method according to claim 2, wherein the slit projection unit and Scheimpflug camera are set up when measuring the axial length of the eye in accordance with the Scheimpflug rule so that the eye is imaged over the complete depth from the cornea up to the retina with sufficient depth of field on the projection plane of the Scheimpflug camera.

4. The method according to claim 1, wherein the thickness of the natural eye lens of the eye or the position of an artificial intraocular lens in the eye which replaces the natural eye lens is derived from the image data sets.

5. The method according to claim 4, wherein the accommodation muscle, which is provided for deforming the natural eye lens or for adjusting an artificial intraocular lens that replaces the natural eye lens, is set in different states of excitation during a series of measurements, so that the natural eye lens is recorded in different deformation states or the artificial intraocular lens is recorded in different positions.

6. The method according to claim 5, wherein a fixation mark is provided in the ophthalmological analysis system, which is fixed on by the patient during a series of measurements, the actual or virtual distance between eye and fixation mark being varied for variable excitation of the accommodation muscle.

7. The method according to claim 6, wherein the virtual distance between eye and fixation mark is varied by adjusting at least one lens in the beam path between fixation mark and eye.

8. The method according to claim 1, wherein the presence of a keratoconus on the cornea is derived from the image data sets.

9. The method according to claim 8, wherein a three-dimensional graph of the corneal thickness is derived from the image data sets for the keratoconus recognition.

10. The method according to claim 8, wherein a three-dimensional geometry of the corneal anterior face is derived from the image data sets for the keratoconus recognition.

11. The method according to claim 8, wherein, for the keratoconus recognition, the derived actual values of the graph of the corneal thickness and/or the derived actual values of the geometry of the corneal anterior face are compared to comparison values predefined in the analysis system, the presence of a keratoconus being derived as a function of the comparison result.

12. The method according to claim 1, wherein a geometry of the anterior chamber of the eyeball between cornea and iris is derived from the image data sets.

13. The method according to claim 12, wherein the arrangement of a phakic intraocular lens in the anterior chamber of the eyeball between cornea and iris is simulated in the analysis system on the basis of the geometry of the anterior chamber of the eyeball.

14. The method according to claim 1, wherein a geometry of the iris and the part of the vitreous humor directly adjoining it are derived from the image data sets.

15. The method according to claim 14, wherein the arrangement of an intraocular lens in the vitreous humor directly behind the iris is simulated on the basis of the geometry of the iris and the directly adjoining part of the vitreous humor.

16. The method according to one of claim 1, wherein during a series of measurements, a raster screen is positioned in the region between slit projection unit and eye, so that the illumination slit is divided by the raster screen into multiple slit sections, which pass through the eye along separate beam paths to form a scattered light pattern.

17. The method according to claim 16, wherein the refractive ratios of the eye lens, particularly the index of refraction of the tissue forming the eye lens, are derived from the image data sets containing the scattered light pattern.

18. The method according to claim 16, wherein the eye is fixed on a fixation point at infinite distance during the series of measurements using a scattered light pattern, the axial length of the eye between cornea and retina being derived from the image data sets containing the scattered light pattern.

* * * * *